US012364607B2

(12) United States Patent
Day et al.

(10) Patent No.: US 12,364,607 B2
(45) Date of Patent: *Jul. 22, 2025

(54) WOUND CARE DEVICE HAVING DYNAMIC BIOACTIVE NANOFIBER SCAFFOLDING

(71) Applicant: MO-SCI CORPORATION, Rolla, MO (US)

(72) Inventors: Thomas E. Day, Rolla, MO (US); Steven B. Jung, Rolla, MO (US); Charanpreet S. Bagga, Basking Ridge, NJ (US)

(*) Notice: Subject to any disclaimer, the term of this patent is extended or adjusted under 35 U.S.C. 154(b) by 1442 days.

This patent is subject to a terminal disclaimer.

(21) Appl. No.: 16/898,796

(22) Filed: Jun. 11, 2020

(65) Prior Publication Data

US 2020/0297493 A1    Sep. 24, 2020

Related U.S. Application Data

(63) Continuation of application No. 16/796,263, filed on Feb. 20, 2020, now Pat. No. 11,850,155, which is a continuation of application No. 15/198,057, filed on Jun. 30, 2016, now Pat. No. 10,596,000, which is a continuation of application No. 13/721,724, filed on Dec. 20, 2012, now Pat. No. 9,402,724, which is a continuation-in-part of application No. 12/437,531, filed on May 7, 2009, now abandoned.

(60) Provisional application No. 61/127,172, filed on May 12, 2008.

(51) Int. Cl.
*A61F 2/28* (2006.01)
*A61L 27/10* (2006.01)
*A61L 27/12* (2006.01)
*A61L 27/42* (2006.01)
*A61L 27/54* (2006.01)
*A61L 27/56* (2006.01)
*A61L 27/58* (2006.01)

(52) U.S. Cl.
CPC ............... *A61F 2/28* (2013.01); *A61L 27/10* (2013.01); *A61L 27/12* (2013.01); *A61L 27/427* (2013.01); *A61L 27/54* (2013.01); *A61L 27/56* (2013.01); *A61L 27/58* (2013.01); *A61F 2002/2835* (2013.01); *A61F 2210/0004* (2013.01); *A61F 2210/0076* (2013.01); *A61L 2430/02* (2013.01)

(58) Field of Classification Search
CPC .................................. A61F 2/28; A61L 27/10
See application file for complete search history.

(56) References Cited

U.S. PATENT DOCUMENTS

| | | |
|---|---|---|
| 5,401,693 A | 3/1995 | Bauer et al. |
| 5,965,125 A | 10/1999 | Mineau-Hanschke |
| 6,416,774 B1 | 7/2002 | Radin et al. |
| 6,451,059 B1 | 9/2002 | Janas et al. |
| 6,517,857 B2 | 2/2003 | Ylanen et al. |
| 7,579,077 B2 | 8/2009 | Dubrow et al. |
| 2005/0169967 A1 | 8/2005 | Gilchrist et al. |

(Continued)

*Primary Examiner* — Brian A Dukert
(74) *Attorney, Agent, or Firm* — Farber LLC

(57) ABSTRACT

A resorbable bone graft scaffold material, including a plurality of overlapping and interlocking fibers defining a scaffold structure, plurality of pores distributed throughout the scaffold, and a plurality of glass microspheres distributed throughout the pores. The fibers are characterized by fiber diameters ranging from about 5 nanometers to about 100 micrometers, and the fibers are a bioactive, resorbable material. The fibers generally contribute about 20 to about 40 weight percent of the scaffold material, with the microspheres contributing the balance.

19 Claims, 8 Drawing Sheets

(56) References Cited

U.S. PATENT DOCUMENTS

2008/0292839 A1  11/2008  Wei et al.
2009/0060961 A1   3/2009  Naruse et al.
2011/0206828 A1   8/2011  Liu et al.

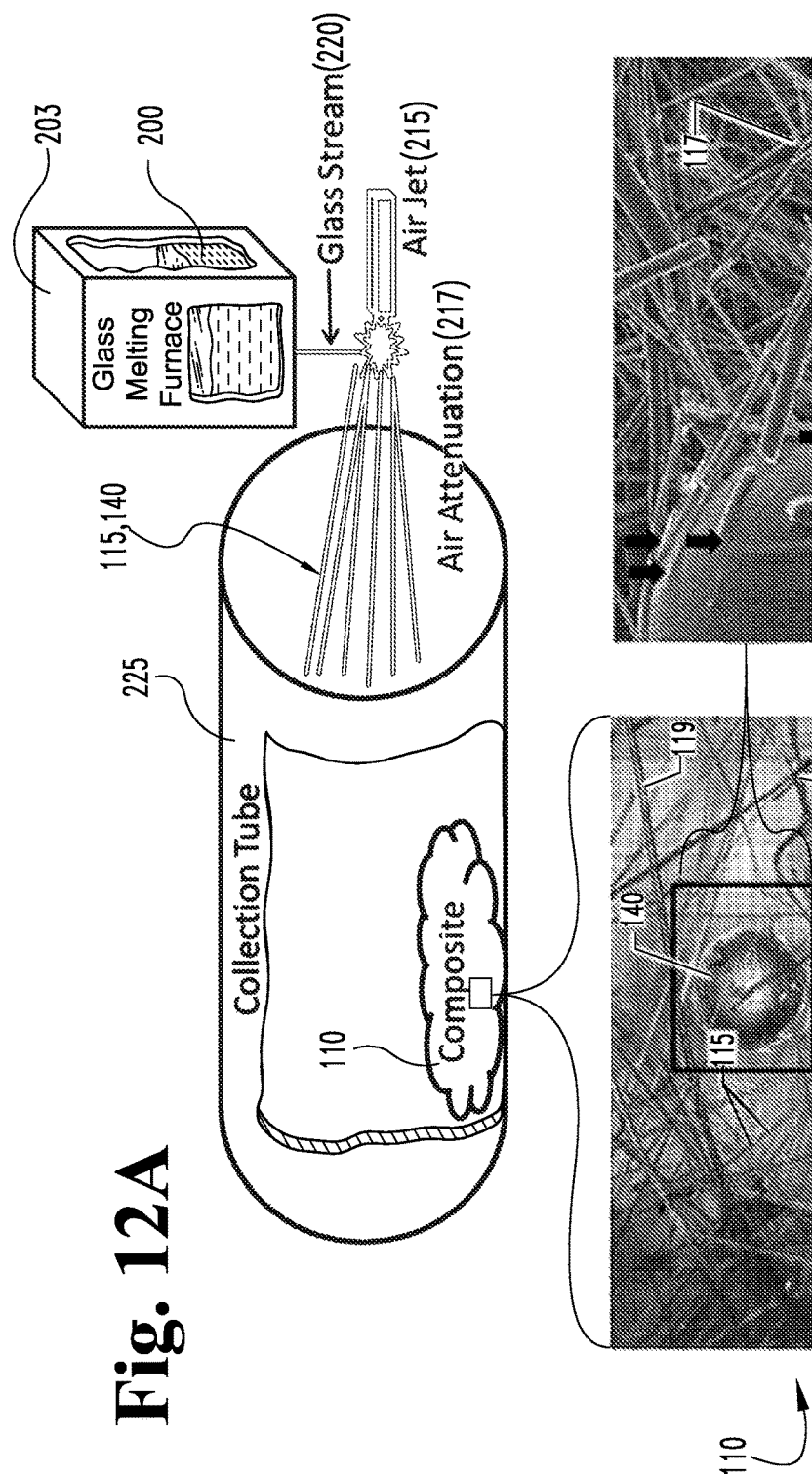
Fig. 12A
Fig. 12B
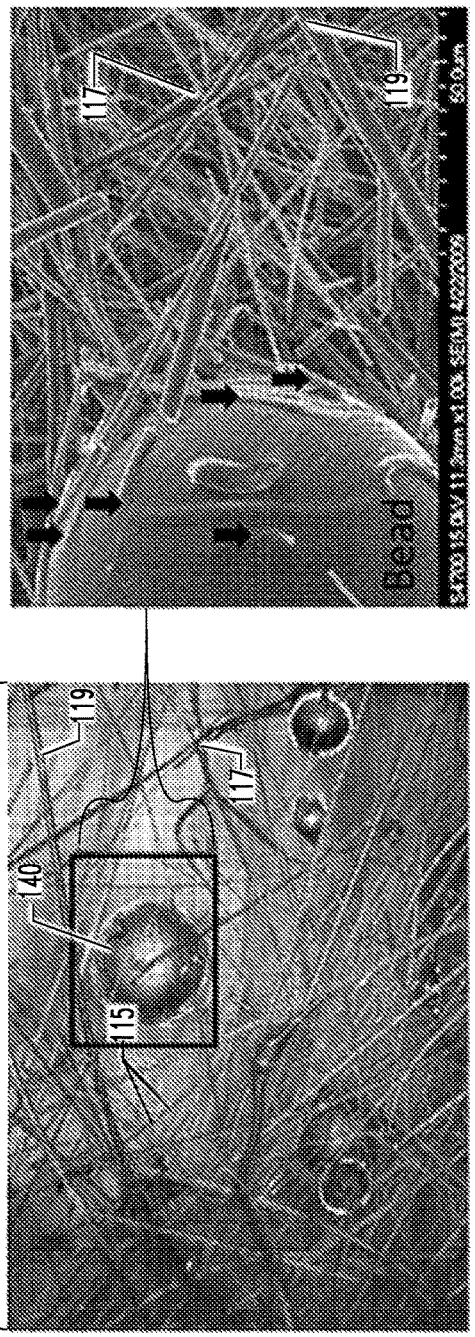
Fig. 12C

WOUND CARE DEVICE HAVING DYNAMIC BIOACTIVE NANOFIBER SCAFFOLDING

CROSS-REFERENCE TO RELATED APPLICATIONS

This application is a continuation of U.S. patent application Ser. No. 16/796,263, filed Feb. 20, 2020, which is a continuation of U.S. patent application Ser. No. 15/198,057, filed Jun. 30, 2016, now U.S. Pat. No. 10,596,000, which is a continuation of U.S. patent application Ser. No. 13/721,724, filed Dec. 12, 2012, now U.S. Pat. No. 9,402,724, which is a continuation-in-part of U.S. patent application Ser. No. 12/437,531, filed on May 7, 2009, now abandoned, which claims priority to and the benefit of U.S. Provisional Patent Application Ser. No. 61/127,172, filed May 12, 2008, the entire contents of which are hereby incorporated by reference.

TECHNICAL FIELD

The present novel technology relates generally to the field of materials science, and, more particularly, to a fibrous scaffolding material and system for bone graft applications.

BACKGROUND

There has been a continuing need for improved bone graft materials. Although autograft materials, the current gold standard for bone grafts, have the acceptable physical and biological properties and also exhibit appropriate structure, the use of autogenous bone also necessarily exposes the patient to multiple surgeries, considerable pain, increased risk, and morbidity at the donor site. Alternately, allograft devices may be used for bone grafts. Allograft devices are processed from donor bone and so also have appropriate structure with the added benefit of decreased risk and pain to the patient, but likewise incur the increased risk arising from the potential for disease transmission and rejection. Autograft and allograft devices are further restricted in terms of variations on shape and size and have sub-optimal strength properties that further degrade after implantation. Further, the quality of autograft and allograft devices is inherently variable, because such devices are made from harvested natural materials. Also, since companies that provide allograft implants obtain their supply from donor tissue banks, supply is uncontrolled since it is limited to the donor pool, which may wax and wane. Likewise, autograft supplies are also limited by how much bone may be safely extracted from the patient, and this amount may be severely limited in the case of the seriously ill and weak.

Since 2001, nearly 150 varieties of bone graft materials have been approved by the FDA for commercial use. Recently, synthetic materials have become an increasingly viable alternative to autograft and allograft devices. Synthetic graft materials have the advantages of not necessitating painful and inherently risky harvesting procedures on patients, have a minimal associated carry risk of disease transmission, and may be strictly quality controlled. Synthetic graft materials, like autograft and allograft, serve as osteoconductive scaffolds that promote the ingrowth of bone. As bone growth is promoted and increases, the graft material resorbs and is eventually replaced with new bone.

Many synthetic bone grafts include materials that closely mimic mammalian bone, such as compositions containing calcium phosphates. Exemplary calcium phosphate compositions contain type-B carbonated hydroxyapatite $[Ca_5(PO_4)_{3x}(CO_3)_x(OH)]$, which is the principal mineral phase found in the mammalian body. The ultimate composition, crystal size, morphology, and structure of the body portions formed from the hydroxyapatite are determined by variations in the protein and organic content. Calcium phosphate ceramics have been fabricated and implanted in mammals in various forms including, but not limited to, shaped bodies and cements. Different stoichiometric compositions, such as hydroxyapatite (HAp), tricalcium phosphate (TCP), tetra-calcium phosphate (TTCP), and other calcium phosphate salts and minerals, have all been employed to match the adaptability, biocompatibility, structure, and strength of natural bone. The role of pore size and porosity in promoting revascularization, healing, and remodeling of bone has been recognized as an important variable for bone grafting materials.

Despite these recent advances, there is a continuing need for synthetic bone graft systems. Although calcium phosphate bone graft materials are widely accepted, they lack the strength, handling and flexibility necessary to be used in a wide array of clinical applications. Heretofore, calcium phosphate bone graft substitutes have been used in predominantly non-load bearing applications as simple bone void fillers and the like. For more clinically challenging applications that require the graft material to take on load, bone reconstruction systems that pair a bone graft material to traditional rigid fixation systems are used. For instance, a resorbable graft containment system has been developed to reinforce and maintain the relative position of weak bony tissue such as bone graft substitutes or bone fragments from comminuted fractures. The system is a resorbable graft containment system composed of various sized porous sheets and sleeves, non-porous sheets and sleeves, and associated fixation screws and tacks made from polylactic acid (PLA). However, the sheets are limited in that they can only be shaped for the body when heated.

In another example, one known bone graft substitute system incorporates flat, round, and oval shaped cylinders customized to fit the geometry of a patient's anatomical defect. This system is used for reinforcement of weak bony tissue and is made of commercially pure titanium mesh. Although this mesh may be load bearing, it is not made entirely of resorbable materials, leaving metal mesh residue in the body after the healing process has run its course.

Thus, there remains a need for resorbable bone grafts with improved handling, flexibility, and compression resistance. The present novel technology addresses this need.

SUMMARY

The present novel technology relates to a biomaterial scaffolding formed from ceramic fibers. One object of the present novel technology is to provide an improved synthetic scaffolding material for bone growth. Related objects and advantages of the present novel technology will be apparent from the following description.

BRIEF DESCRIPTION OF THE DRAWINGS

FIG. 12A is a schematic illustration of a melt-blown process for glass fiber production.

FIG. 12B is a photomicrograph of a melt-blown glass fiber material as produced by the process of FIG. 12A.

FIG. 12C is an enlarged photomicrograph of the composite of FIG. 12B showing a glass sphere enmeshed in glass fibers.

DETAILED DESCRIPTION OF THE PREFERRED EMBODIMENT

Figure 1:
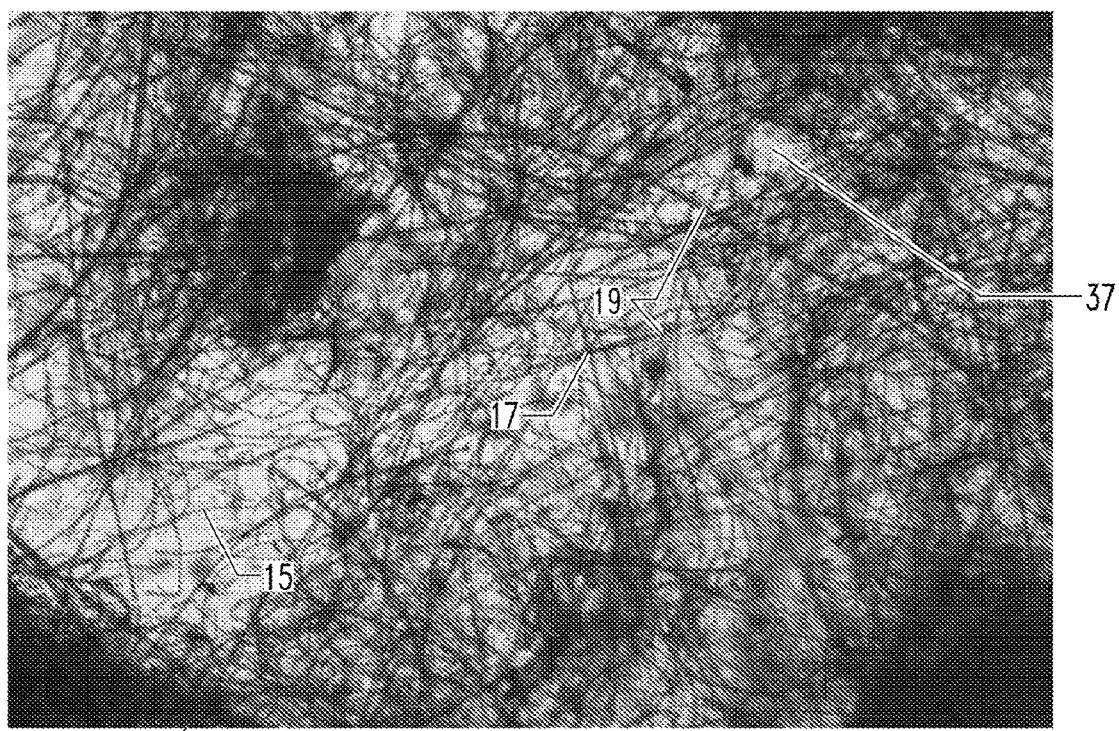
FIG. 1. is a first photomicrograph of a dynamic biomaterial scaffold according to a first embodiment of the present novel technology.
Figure 2:
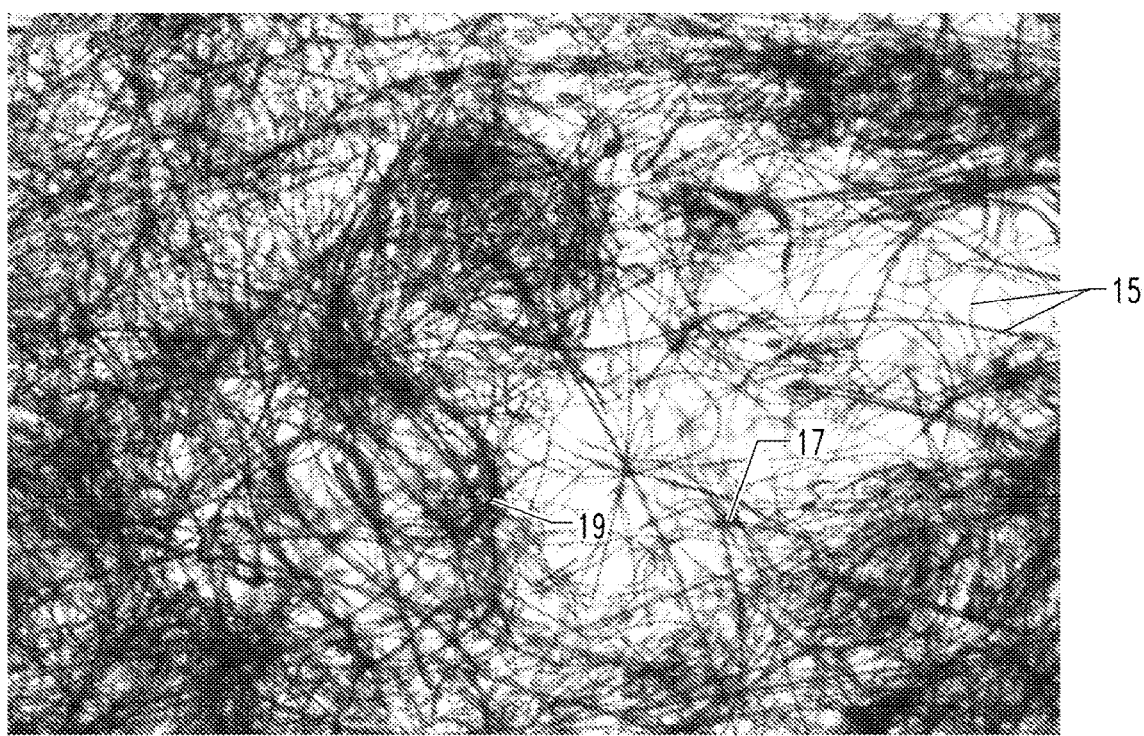
FIG. 2. is a second photomicrograph of a dynamic biomaterial scaffold according to a first embodiment of the present novel technology.
Figure 3:
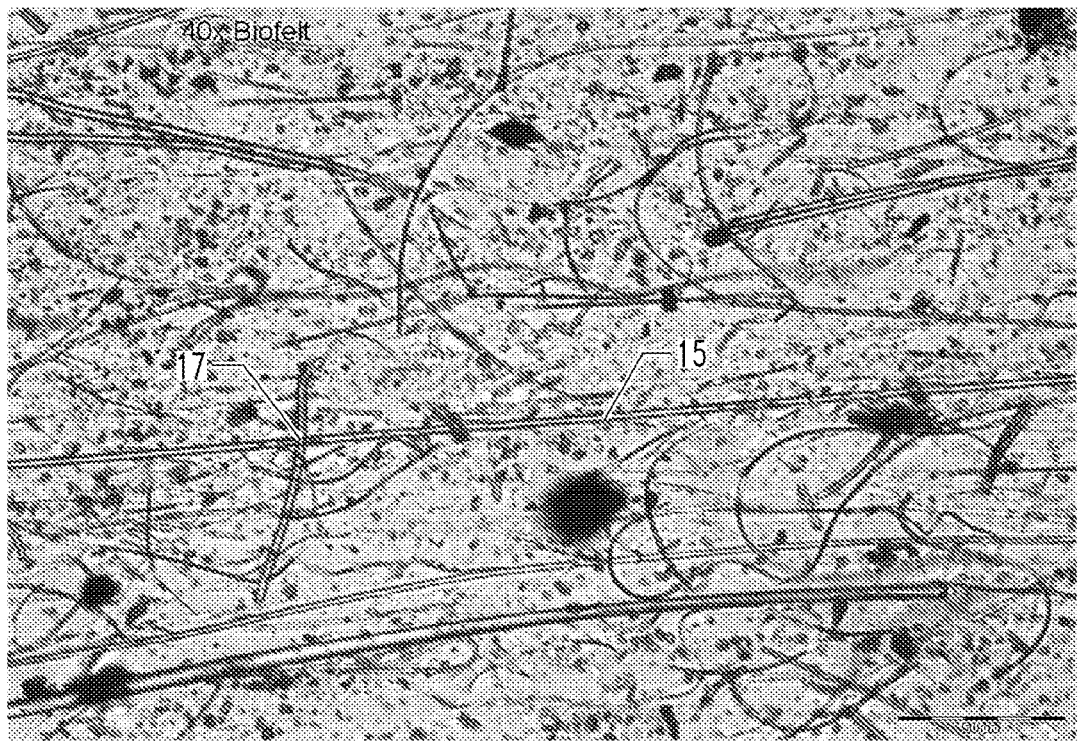
FIG. 3. is a third photomicrograph of fibers as found in FIG. 1.
Figure 4:
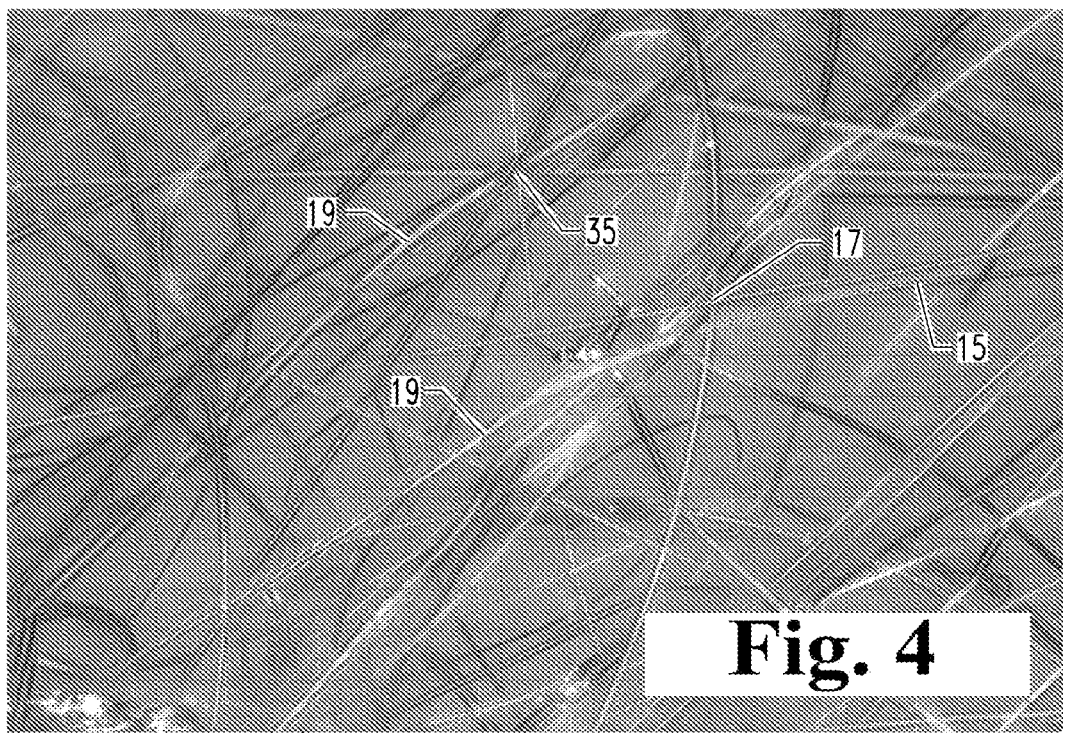
FIG. 4 is a fourth photomicrograph of fibers as found in FIG. 1.
Figure 5:
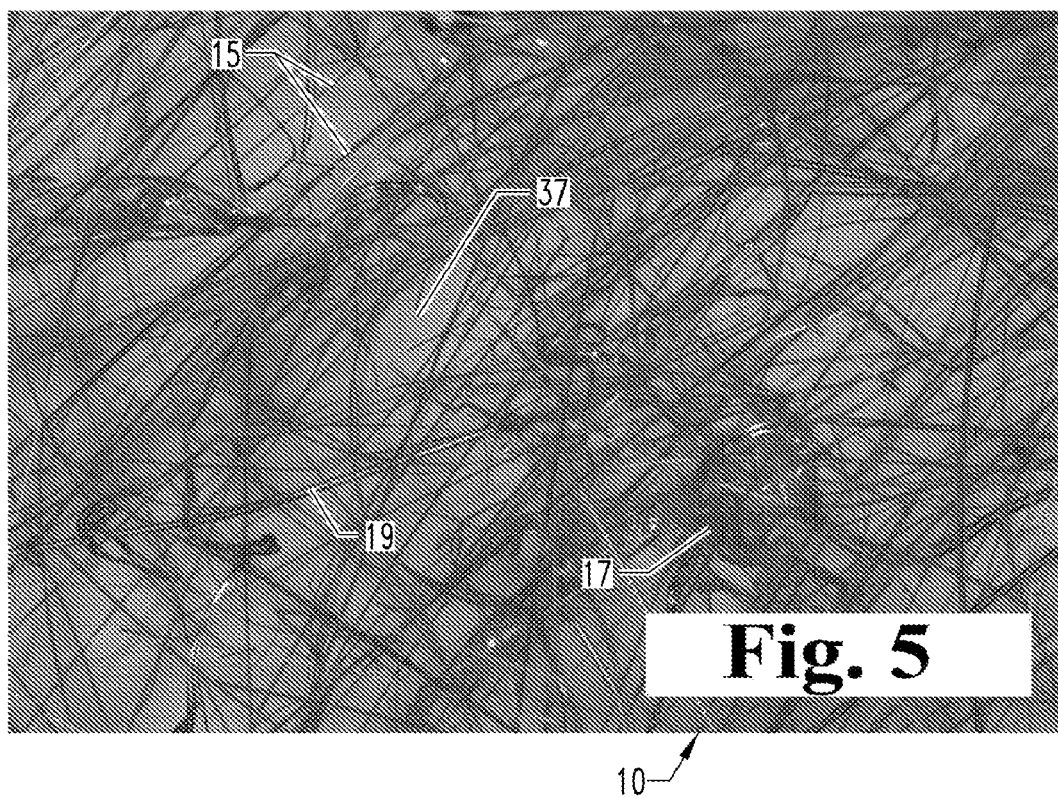
FIG. 5 is a fifth photomicrograph of fibers as found in FIG. 1.

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

The current use of specific biomaterial scaffolds as mediators in the healing process of biologic tissues (both hard bone and soft cartilage) has lead to significant increases in the understanding of the requirements and process of healing with synthetic materials. The job of a scaffold is to provide a three-dimensional framework upon which cells of the appropriate phenotype (such as osteoblasts for bone and chondrocytes for cartilage) can attach, express relevant signaling molecules and begin the process of tissue formation. Scaffolds typically serve to accommodate the natural healing process by affording the attachment of initial proteins, the release of signals from egressing cells, and/or the creation of the new, de novo, tissue in the structure needed and dictated by physiologic feedback mechanisms. The microenvironment of a scaffold influences its behavior and tissue interactions from the initiation to the final stages of healing. Complete vascularity, remodeling and ultimate structure of the scaffold-tissue interactions influences the degree of success or failure of the resulting physiologic tissue.

FIGS. 1-5 illustrate a first embodiment bioactive nanofiber scaffold 10 according to the present novel technology. The scaffold 10 is made up of a plurality of partially interlocking and, more typically, interlinking fibers 15 defining a three-dimensional porous support scaffold or web 10. The support web 10 is made up of biomaterial fibers 10 that are interlinked or interwoven, and some may be fused at their intersections 17. At least some of the interlinked fibers 15 may thus move over one another with some degree of freedom, yielding a support web 10 that is dynamic in nature. The composition of the fibers 15 used as the struts 19 of the resulting dynamic nanoscaffold 10 are typically solid, non-porous pure bioactive glass, ceramic or glass-ceramic formulations, such that within the range of fiber diameter and construct size, that the scaffolding fibers 15 are generally characterized as having the attributes of bioactivity. In other words, the glass or like ceramic fibers 15 will react with physiologic fluids in vivo to promote bone apposition and/or tissue apposition, and ultimately, within a reasonable timeframe after the healing process has run its course, be substantially resorbed from the body. These glass/ceramic fibers 15 are typically free of polymer fillers (especially long-chain polymers) or like materials, as such organic materials are both unnecessary to their production and cannot withstand the formation temperatures experience by the ceramic fibers 15.

The diameters of the fibers 15 defining the dynamic scaffold 10 are typically sufficiently small to allow for inherent interlinking of the resulting three-dimensional scaffold 10 upon itself, without the need for sintering, fusing or otherwise attaching the fibers 15 to one another at their intersections 17, although some such fusing or attachment may be employed to further stiffen the scaffold 10 if desired. Hence the scaffold 10 is self constrained to not completely fall apart, yet the individual fibers 15 defining the support struts 19 are free to move small distances over each other to grant the scaffold 10 its dynamic qualities such that it remains flexible while offering sufficient support for tissue formation and growth thereupon. As will be described in detail below, pluralities of fibers 15 characterized as substantially having diameters below 1 micrometer (1000 nanometers) are sufficient to form dynamic scaffolding 10, as are pluralities of fibers 15 characterized as substantially having diameters below 100 nanometers. The scaffolding 10 may also be constructed from a plurality of fibers 15 having multi-modal diameter distributions, wherein combinations of diameters may be employed to yield specific combinations of dynamic flexibility, structural support, internal void size, void distribution, compressibility, dissolution and resorption rates, and the like. Typically, the ranges of fiber diameters within a construct typically ranging from less than about 1 micron (submicron) up to about 100 microns; more typically, fiber diameters range from about 0.5 microns to about 10 microns; still more typically, fiber diameters range from about 0.5 to about 6 microns; yet more typically, fiber diameters range from 0.5 to about 2 microns; still more typically, fiber diameters range from about 1 micron to about 6 microns. In all cases, predetermined amounts of larger fibers may be added to vary one or more of the properties of the resultant scaffolding 10 as desired. It should be noted that as the amount of smaller (typically less than 10 micrometer) diameter fibers 15 decreases and more of the scaffolding construct 10 contains fibers 15 of relatively greater diameters, the entire construct 10 typically tends to become less self constrained. Thus, by varying the relative diameters and aspect ratios of constituent fibers 15 the resulting scaffold structure 10 may be tailored to have more or less flexibility and less or more load-bearing rigidity.

Figure 6A:
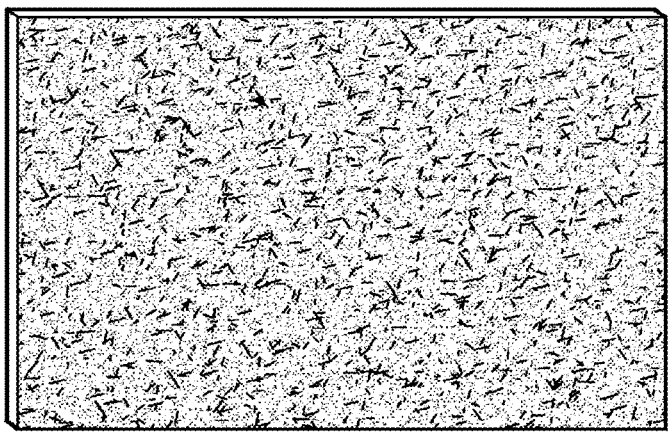
FIG. 6A is a perspective view of a first interlocking, entangled macroscaffold construct formed of the fibrous biomaterial scaffold of FIG. 1.
Figure 6B:
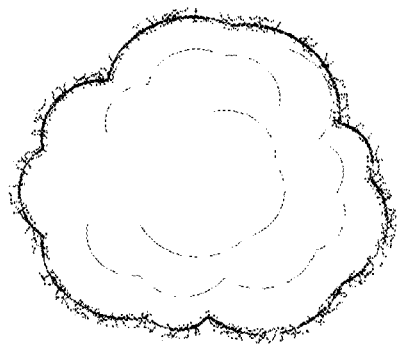
FIG. 6B is a perspective view of a second interlocking, entangled macroscaffold construct formed of the fibrous biomaterial scaffold of FIG. 1.
Figure 6C:
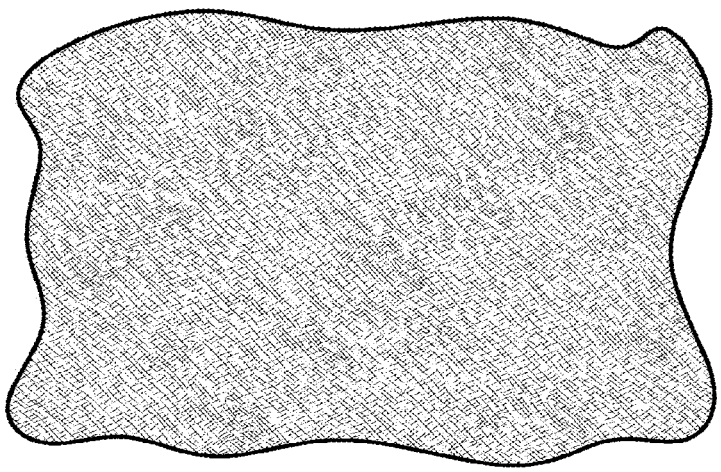
FIG. 6C is a perspective view of a third interlocking, entangled macroscaffold construct formed of the fibrous biomaterial scaffold of FIG. 1.
Figure 7:
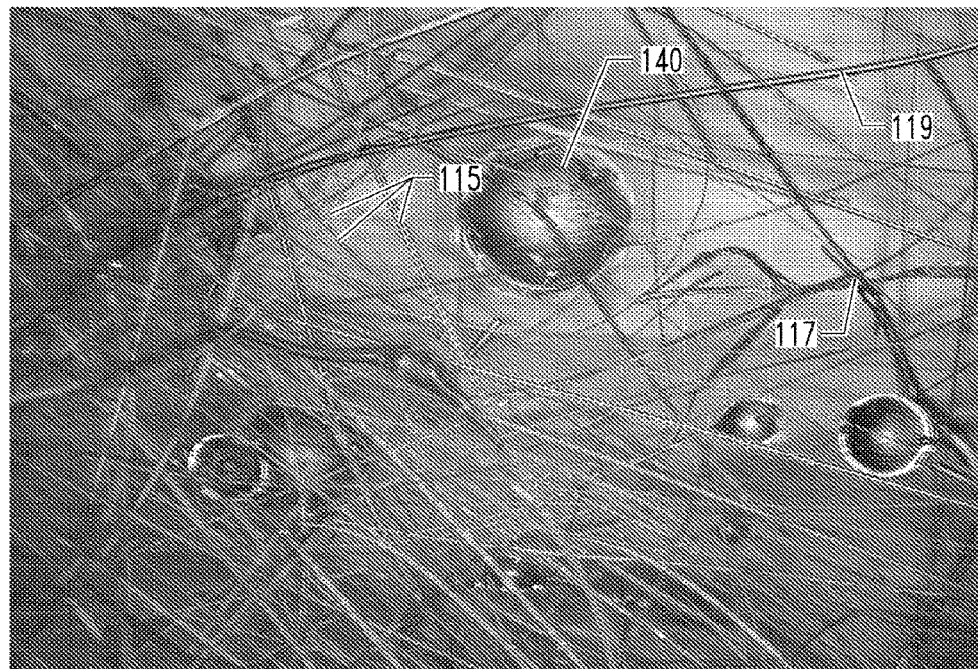
FIG. 7 is a first photomicrograph of a dynamic biomaterial scaffold including glass microspheres according to a second embodiment of the present novel technology
Figure 8:
FIG. 8 is a second photomicrograph of the embodiment of FIG. 7.
Figure 9:
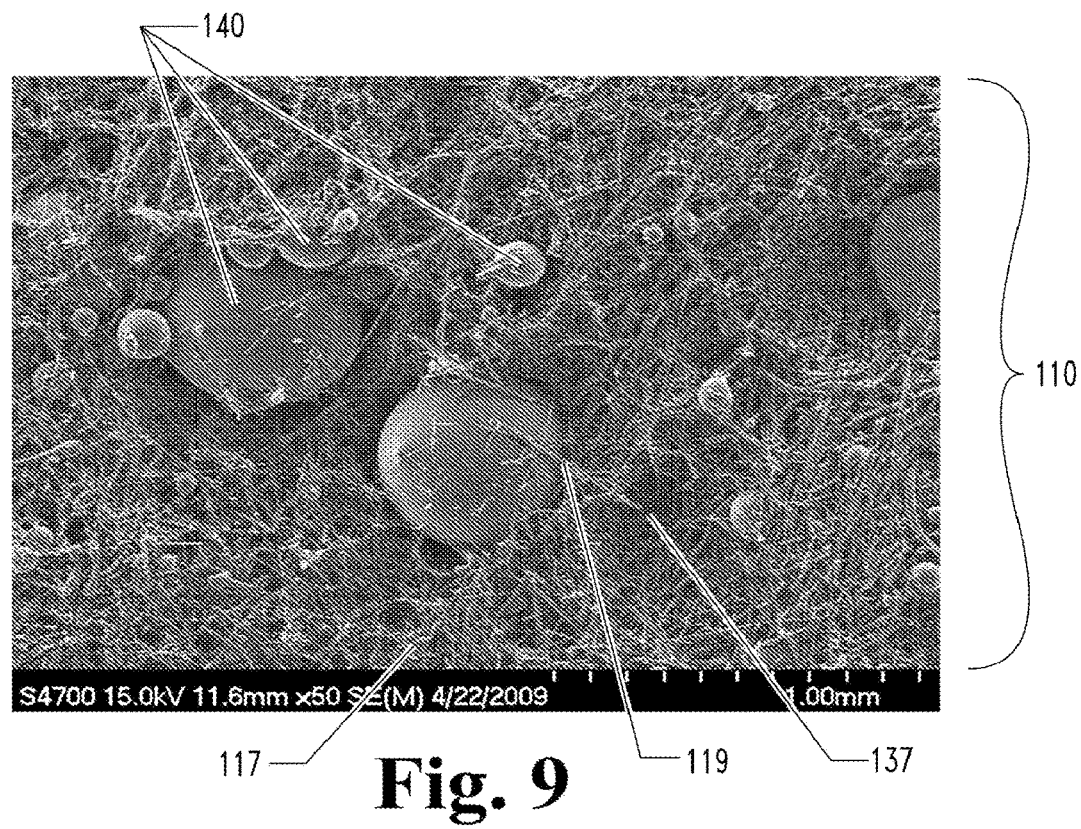
FIG. 9 is a third photomicrograph of the embodiment of FIG. 7.
Figure 10:
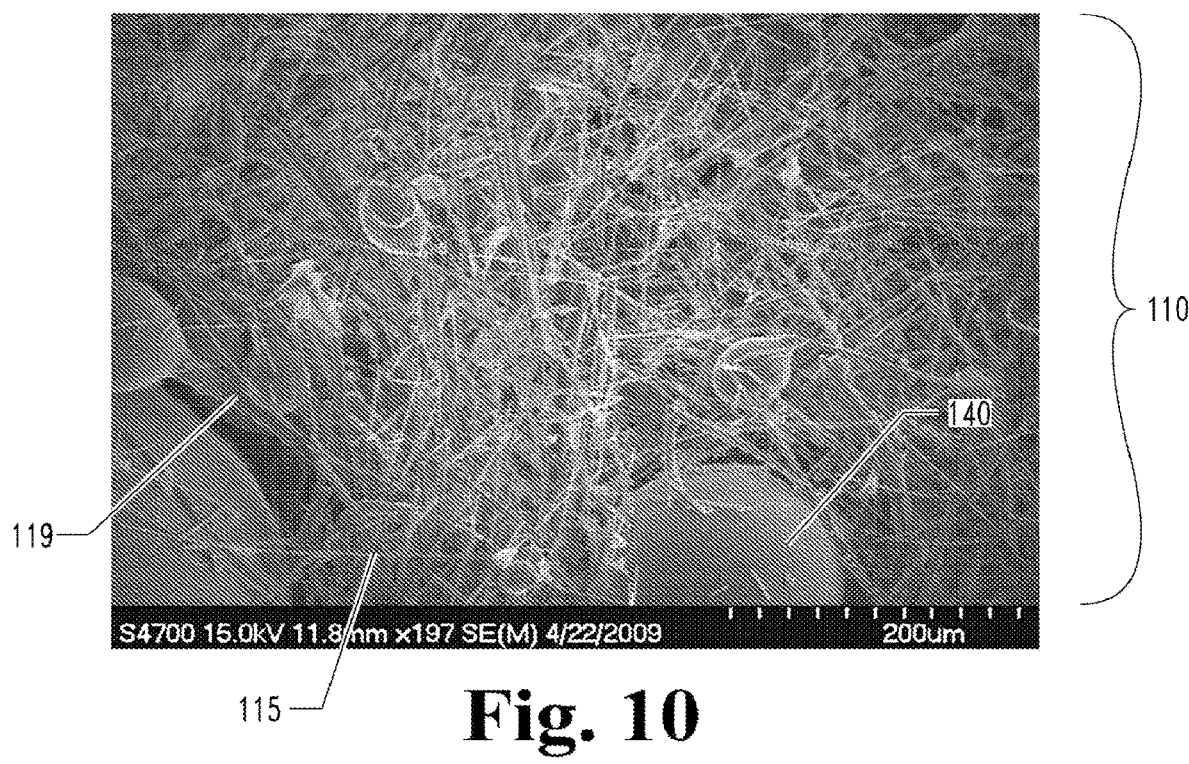
FIG. 10 is a fourth photomicrograph of the embodiment of FIG. 7.
Figure 11:
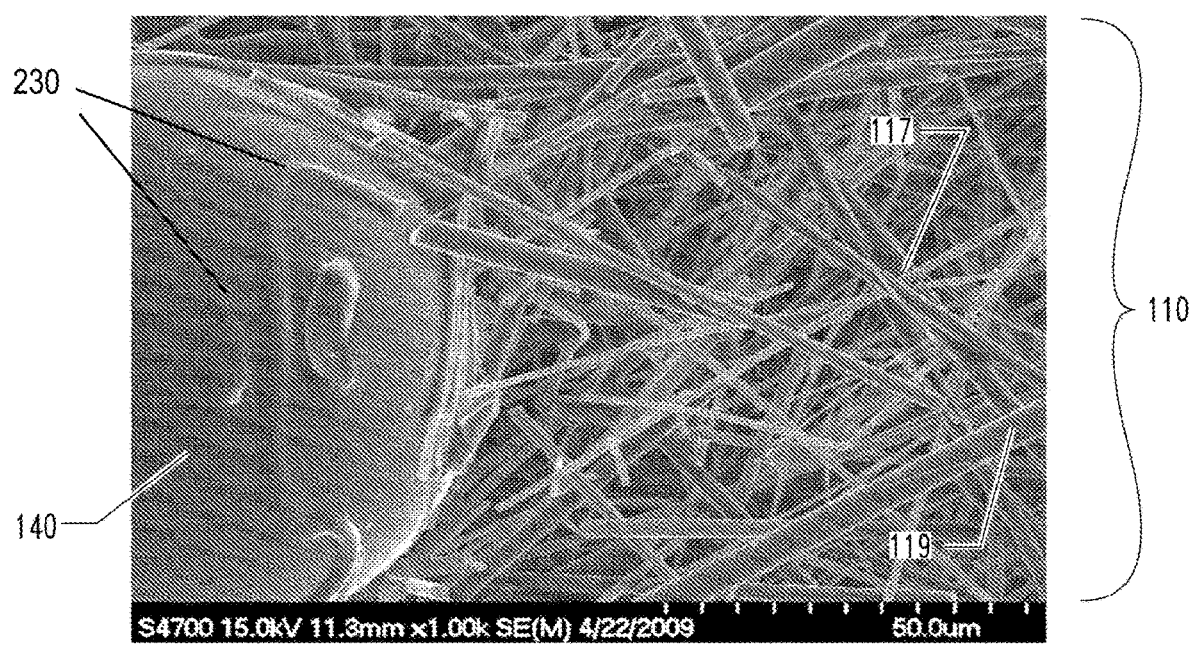
FIG. 11 is a fifth photomicrograph of the embodiment of FIG. 7.

One factor influencing the mechanism of a dynamic scaffold 10 is the incorporation of relatively small diameter fibers 15 and the resulting support macrostructure 20. Fiber scaffolds 10 may be made by a variety of methods resulting in an interlinking, partially interlocking, entangled, and/or specifically orientated three-dimensional fiber construct 20 (see FIGS. 6A-6C). These fibers 15 are not necessarily continuous, but may be short and discrete, or some combination of long, continuous fibers 15 and short, discrete fibers 15. The fibers 15 intersect are another way to define intersections 17 and also to define pores or voids 37. The resulting support macrostructure or device 20 may thus be a nonwoven fabric made via a spunlaid or spun blown process, a melt blown process, a wet laid matt or 'glass tissue' process, or the like and may be formed to have the characteristics of a felt, a gauze, a cotton ball, cotton candy, or the like. Typically, the fibers 15 are formed from a molten bioactive glass precursor through a melt-blown process; more typically, the glass melt precursor is a 45S5 bioactive glass.

The fibers 15 defining the scaffold construct 20 typically have non-fused linkages 35 that provide subtle flexibility and movement of the scaffolding 10 in response to changes in its environment, such as physiological fluctuations, cellular pressure differences, hydrodynamics in a pulsatile healing environment, and the like. This in vivo environment can and will change over the course of the healing process, which may last as long as several months or even longer. The scaffold 10 typically retains its appropriate supportive characteristics and distribution of pores 37 throughout the healing process such that the healing mechanisms are not inhibited. During the healing process, the pores 37 defined by the matrix of interlinking and tangled fibers 15 may serve to carry biological fluids and bone-building materials to the site of the new bone growth. The fluids likewise slowly dissolve fibers 15 made of bioactive glass and the like, such that the scaffolding 10, and particularly the pores 37, changes in size and shape in dynamic response to the healing process.

Scaffolds 10 are typically provided with a sufficiently permeable three-dimensional microstructure for cells, small molecules, proteins, physiologic fluids, blood, bone marrow, oxygen and the like to flow throughout the entire volume of the scaffold 10. Additionally, the dynamic nature of the scaffold 10 grants it the ability to detect or respond to the microenvironment and adjust its structure based on forces and pressure exerted elements within the microenvironment.

Additionally, scaffolds 10 typically have sufficient three-dimensional macrostructure for compliance of the macroscaffold support device 20 when physically placed into an irregular shaped defect, such as a void, hole, or tissue plane as are typically found in bone, tissue, or like physiological site. The device 20 typically experiences some degree of compaction upon insertion into the defect, while the permeable characteristics of the microstructure are maintained. Typically, as with the placement of any bone void filler, than the device 20 remains within 2 mm of the native tissue in the defect wall.

Physical macroforms or devices 20 made from the scaffolding 10 can appear similar to felts, cotton balls, textile fabrics, gauze and the like. These forms have the ability to wick, attach and contain fluids, proteins, bone marrow aspirate, cells, as well as to retain these entities in a significant volume, though not necessarily all in entirety; for example, if compressed, some fluid may be expulsed from the structure.

Another advantage of the macroscaffolding devices 20 is their ability to modify or blend the dynamic fiber scaffolds 10 with a variety of carriers or modifiers to improve handling, injectability, placement, minimally invasive injection, site conformity and retention, and the like while retaining an equivalent of the 'parent' microstructure. Such carriers ideally modify the macro-scale handling characteristic of the device 20 while preserving the micro-scale (typically on the order of less than 100 micrometers) structure of the scaffolding 10. These carriers resorb rapidly (typically in less than about 2 weeks; more typically in less than about 2 days) without substantially altering the form, microstructure, chemistry, and/or bioactivity properties of the scaffolding. These carriers include polaxamer, glycerol, alkaline oxide copolymers, bone marrow aspirate, and the like.

Example 1

A tissue growth support device 20 may be constructed from nanofiber scaffolding 10 by spin blowing fibers 15 characterized with diameters typically less than about 0.1 micrometer into a felt-like fabric. The fibers are typically randomly orientated to produce a substantially densely packed textile and is characterized as having a relatively fine pore volume as defined by the interstices or pores 37 between the fibers 15. The device 20 typically has the form of a thin, stiff sheet and may be cut or otherwise shaped as desired.

Example 2

A plurality of interlocking fibers 15 are spun or blown into a randomly-oriented assemblage 20 having the general appearance of a cotton ball. The fibers 15 are typically characterized as having diameters of from less than about 1000 nm (1 micrometer) ranging up to approximately 10,000 nm (10 micrometers). The resulting cotton-ball device 20 may be formed with an uncompressed diameter of typically from between about 1 and about 6 centimeters, although any convenient size may be formed, and may be compressible down to between about ½ and ¼ of its initial size. The device 20 substantially returns to its original size and shape once the compressive forces are removed. By varying the relative diameters of some of the fibers 15, structures ranging from 'cotton ball' to 'cotton candy' may be produced, with varying ranges of fiber diameters from less than about 10 nm to greater than about 10 microns.

Example 3

Fibers 15 may be woven, knitted, or otherwise formed into a fabric device 20 having a gauze-like consistency. The fibers 15 are typically greater than about one micrometer in diameter and may be as large as about 100 micrometers in diameter. The micro-scale orientation of the fibers 15 is typically random, although the fibers may be somewhat or completely ordered. On a macro-scale, the fibers 15 are typically more ordered. The constituency of these devices 20 may have varying amounts of smaller fibers 15 incorporated therein to maintain the self constrained effect.

FIGS. 7-11 illustrate another embodiment of the present novel technology, a bioactive nanofiber scaffold 110 as described above with respect to FIGS. 1-6, but having ceramic or, more typically, glass microspheres, beads or shot 140 distributed therethrough. The glass shot 140 is typically made of the same general bioactive composition as the fibers 115, but may alternately be made of other, different bioactive compositions. The glass shot 140 is typically generally spherical, but may have other regular or irregular shapes. The glass shot 140 typically varies in size, having diameters ranging from roughly about the width of the fibers 115 (more typically, the struts 119) to diameters orders of magnitude greater than the typical fiber widths. While smaller shot may tend to lodge in or around fiber intersections 117, larger shot tend to become embedded in the scaffolding device 120 itself and held in place by webs of fibers 115. Pore-sized microspheres may tend to lodge in pores 137. One function of shot 140 is to preserve pore structure and distribution upon in vivo insertion and compaction of scaffolding device 120. Spheres 140 also function to interact with nanofiber matrix 110 to allow scaffolding 120 to be formed into and hold a new shape; in other words, interactions of fibers 115 and spheres 140 give rise to shapeability of scaffolding device 120.

The glass shot 140 may be composed of a predetermined bioactive material and tailored to dissolve over a predetermined period of time when the scaffolding 110 is placed in vitro, so as to release a predetermined selection of minerals, bone growth media, and the like at a predetermined rate. Likewise, the glass shot 140 may be hollow bioactive glass, polymer or the like microspheres defining inner core volumes respectively filled with specific mixture of medicines, nutritive supplements, antibiotics, antivirals, vitamins, mixtures thereof, or the like to be released at and around the bone regrowth site at a predetermined rate and for a predetermined length of time. The release rate and duration of release may be functions of shot size and wall thickness as well as the distribution function of the same.

FIG. 12 details the melt blown process as typically used to produce the scaffold device 120. A melt 200 of bioactive glass is prepared, either from a batch, from melting already prepared bioactive glass frit, or a combination of the two. Air attenuation 215 is used to impact and disrupt a stream 220 of melt derived bioactive glass to yield a composite mixture 110 of glass beads 140 and glass fibers 115. The glass melt 200 is bottom drained from a melter and compressed air 215 is directed, typically perpendicular, to the stream 220 in the direction of a collection area 225, typically a steel tube or the like. Fibers 115 and beads 140 are generated simultaneously during air attenuation 215, so the bulk composite material 20 is a collection of fibers 115 and beads 140 that impacted one another during the process in a molten state and formed a three dimensional glass composite 110.

The beads 140 typically have a greater mass than the fibers 115, and so retain heat longer, solidify later, and therefore tend to flow around and/or bond to multiple fibers 115 during the melt blown process. Typically, the beads 140 become an integral part of the composite 110 and do not simply fall out when the device 120 is handled. The multiple fusion points 230 between the fibers 115 and the beads 140 increase the overall strength of the material 110 and even when compressed or handled, the beads 140 typically stay embedded in the fiber matrix 110, yielding an advantage over simply adding individual glass beads 140 to a bundle of fibers 15 because the materials 140, 15 are not bonded together. Even electrospun fibers 15 that may form some beads 140 during the electrospinning process do not form multiple bonds during the drying/curing processes and do not exhibit the advantages of the composite 110. If a bundle of fibers 15 and loose beads 140 were to be heated high enough to viscously flow the glass and bond the fibers 15 and beads 140, the fibers 15 would likewise bond to each other along with the beads 140 and the resulting composite would thus be rigid and inflexible. In contrast, the instant composite material 110 has beads 140 that are bonded to multiple fibers 115, while the fibers 115 themselves are generally not bonded to each other. This allows the fibers 115 to move relatively freely over one another, at least for short distances, affording the material 110 flexibility but also keeping the beads 140 dispersed and intact inside the composite 110.

The air attenuation process 215 allows for tailoring the composite 110 makeup by varying the relative bead 140 and fiber 115 content, the bead 140 and fiber 115 size distributions, the bulk density of the composite 110, and the dissolution rate of the final composite 110. This is done by controlling the parameters of the process such as the melt temperature, the molten stream diameter, air stream pressure, distance from the air nozzle to the glass stream, the shape of the air (i.e., flat vs. round), the distance from the air attenuation in which the composite is collected, and the like. These parameters allow for significant control and modification of the properties of the composite 110 and can yield a variety of different types of materials.

Movement of the fibers 115 is desired for the fibers 115 to be able to act as a carrier for the glass beads 140, since the fibers 115 typically make up, at most, 40 weight percent of the composite 110, typically contributing 20 weight percent or less in some applications. Such a great quantity of beads (i.e., typically more than about 60 weight percent, more typically, more than about 80 weight percent) cannot be contained by fibers 115 if they are not at least partially bonded together. The ability for the composite 110 to be molded and/or compressed without degrading the composite 110 (such as breaking loose the beads 140 from the fiber matrix 110) lends versatility to the application the composite 110 may enjoy.

For applications of wound or burn care, a composite device 120 of 60 weight percent beads 140 and 40 weight percent fiber 115 with a bulk density of >0.1 g/cc is desirable for some glass compositions, while a composite of about 90 weight percent beads 140 and about 10 weight percent fibers 115 is optimal for other glass compositions, with a bulk density of about 0.5 g/cc. This variance arises because bioactive glass dissolution rates are tailorable, so depending on the time a dressing is desired to be in contact with a wound, the glass composition and composite 120 composition can vary. For typical wound care, a glass composition that dissolves in a matter of days is advantageous because it corresponds with normal managed wound care (2 to 3 times weekly). Other wound applications, especially military may require the dressing to be more chemically durable in an urban environment, and especially if the dressing is being used for hemostasis or blood loss control.

Orthopedic implants have both different duties and different requisite properties than soft tissue dressings, and require different composite properties because they are placed in the bone defect prior to closure of the wound, so a composite device 120 made up of about 80 weight percent beads 140 and about 20 weight percent fiber 115 with a bulk density of >1.0 g/cc is more appropriate. From these examples, one skilled in the art would appreciate the need for a material to have the ability to be compressed over a wide range of bulk densities while retaining the components of the composite. Glass is often thought of as a rigid and fragile material, and this composite 110 is distinctly different from the known art insofar as it allows significant compression and flexibility while not damaging the material as a whole. Achieving this sort of a flexible and tailorable composite 110 with a family of melt derived bioactive glass materials that are proven effective for healing hard and soft tissue is novel.

A typical device 120 will typically include between about 60 and about 95 weight percent beads 140. The beads will typically be present in a typically bell-curve distribution ranging between 30 microns to 3 mm, with 50 weight percent under 500 microns and 90 weight percent under 1.4 mm. The bulk density (usable/effective) is typically about 0.1 to about 0.5 g/cc for soft tissue applications and between about 0.8 g/cc to about 1.5 g/cc, more typically from about 1 g/cc to about 1.4 g/cc, and even more typically between about 1.1 g/cc to about 1.3 g/cc for bone applications. A typical graft size range is from about 0.5 cc to about 20 cc, more typically between about 3 cc and about 10 cc for bone. A soft tissue dressing typically varies in size from about 0.1 cc to about 300 cc or more, depending on the application. The degradation rate for orthopedic applications is typically, by weight, may be expressed as a maximum of 70% unreacted graft after 4 weeks, 50% unreacted graft in 8 weeks, and 20% unreacted graft after 12 weeks in a bone void with <5% graft remaining after 24 weeks. The fiber carrier is typically greater than 90 percent reacted in 1 to 4 weeks, more typically in 2 to 3 weeks.

EXAMPLE

A scaffold device 120 composed of melt derived bioactive glass beads 140 with a generally randomly interwoven, interlinked, and physically bonded fiber carrier matrix 115 of generally the same composition. The fibers 115 are typically substantially between 1 micron and 30 microns in diameter, and are between about 5 weight percent and about 30 weight percent of the device 120. The glass beads 140 typically connect to the fibers 115 in multiple locations, with a plurality of fibers 115 typically connecting to each bead 140. The scaffold device 120 is typically pliable, flexible, and formable, especially after being wetted by blood, bone marrow aspirate, or other bodily fluids. Multiple fibers 115 are bonded to the glass beads 140, hence making the composite 140 more durable and resistant to breaking due to forming and compression.

In some embodiments, the fibers 115 may be crystallized or partially crystallized.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

We claim:

1. A wound care device, comprising:
a porous, pliable and formable support matrix comprising a plurality of overlapping and entangled solid, polymer-free bioactive, resorbable ceramic fibers, each respective fiber having a diameter ranging from about 5 nanometers to about 100 micrometers;
a plurality of pores distributed throughout the support matrix; and
a plurality of bioactive, resorbable glass or ceramic beads distributed throughout the support matrix;
wherein the wound care device is configured to be sufficiently chemically durable to reduce or stop blood loss from the wound.

2. The wound care device of claim 1, wherein the beads contribute about 60 weight percent and the fibers contribute about 40 weight percent of the support matrix,
further wherein the support matrix has a bulk density of greater than about 0.1 g/cc for blood treatment applications.

3. The wound care device of claim 1, wherein the beads contribute about 90 weight percent and the fibers contribute about 10 weight percent of the support matrix,
further wherein the support matrix has a bulk density of greater than about 0.5 g/cc for blood treatment applications.

4. The wound care device of claim 1, wherein the fibers are composed of a material selected from the group including calcium phosphate, hydroxyapatite, bioactive glass and combinations thereof.

5. The wound care device of claim 1, wherein the beads are solid and wherein the beads have the same composition as the fibers.

6. The wound care device of claim 1, further including a medicine, a nutritive supplement, an antibiotic, an antiviral, a vitamin, or a combination thereof.

7. The wound care device of claim 1, wherein at least some of the respective beads are fused to at least one respective fiber.

8. The wound care device of claim 1, wherein the fiber diameters are substantially between about 10 nanometers and about 10 micrometers.

9. The wound care device of claim 1, wherein at least some of the fibers are fused together.

10. The wound care device of claim 1, wherein the beads have diameters ranging from about 30 microns to about 3 millimeters.

11. The wound care device of claim 1, further comprising a carrier.

12. The wound care device of claim 11, wherein the carrier is selected from the group consisting of polaxamer, glycerol, alkaline oxide copolymers, and bone marrow aspirate.

13. The wound care device of claim 1, wherein the fibers are randomly oriented with respect to each other.

14. The wound care device of claim 1, wherein the fibers have varying diameters.

15. The wound care device of claim 1, wherein at least some of the fibers are nanofibers.

16. The wound care device of claim 1, wherein the beads have varying sizes.

17. The wound care device of claim 1, wherein some of the fibers are fused to some of the beads.

18. The wound care device of claim 1, wherein the fibers are interlinked to form a fibrous, self-constrained construct, some of the fibers being freely movable over other fibers of the construct.

19. The wound care device of claim 1, further having a formed, regular shape including a sheet.

* * * * *